United States Patent
Azizinamini et al.

(10) Patent No.: US 11,953,492 B1
(45) Date of Patent: *Apr. 9, 2024

(54) IN SITU RAPID TESTING FOR ASSESSING QUALITY OF CONCRETE

(71) Applicants: Atorod Azizinamini, Miami, FL (US); Amer I. Awwad, Miami, FL (US)

(72) Inventors: Atorod Azizinamini, Miami, FL (US); Amer I. Awwad, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/477,672

(22) Filed: Sep. 29, 2023

Related U.S. Application Data

(62) Division of application No. 18/307,600, filed on Apr. 26, 2023, now Pat. No. 11,828,744.

(51) Int. Cl.
  *G01N 33/38* (2006.01)
  *G01N 3/06* (2006.01)
  *G01N 3/12* (2006.01)

(52) U.S. Cl.
  CPC ............. *G01N 33/383* (2013.01); *G01N 3/06* (2013.01); *G01N 3/12* (2013.01); *G01N 2203/0298* (2013.01)

(58) Field of Classification Search
  CPC .......... G01N 33/383; G01N 3/06; G01N 3/12; G01N 2203/0298
  See application file for complete search history.

(56) References Cited

U.S. PATENT DOCUMENTS

| | | |
|---|---|---|
| 4,979,390 A | 12/1990 | Schupack et al. |
| 11,680,884 B2 | 6/2023 | Zhang et al. |
| 2023/0123095 A1 | 4/2023 | Liu et al. |

FOREIGN PATENT DOCUMENTS

| | | |
|---|---|---|
| CN | 108982327 | 12/2018 |
| CN | 109596814 | 4/2019 |

*Primary Examiner* — Jonathan M Dunlap
(74) *Attorney, Agent, or Firm* — Saliwanchik, Lloyd & Eisenschenk

(57) ABSTRACT

Systems and methods are provided to simulate, approximate, or replicate conditions similar to concrete elements being placed under pressures equivalent to several hundred feet of ocean water and to provide information useful to assess relative durability of concrete without coring or other destructive actions. The quality of concrete can be assessed by measuring the pressure drop of water or other liquid to ingress through the concrete surface under high pressure over time. A rapid assessment of quality of existing concrete is provided. Systems and methods can efficiently assess long term durability of existing concrete elements such as those used in midrise buildings, parking garages, bridge decks, and the like.

20 Claims, 20 Drawing Sheets

IN SITU RAPID TESTING FOR ASSESSING QUALITY OF CONCRETE

CROSS-REFERENCE TO RELATED APPLICATION

The present application is a divisional application of U.S. application Ser. No. 18/307,600, filed Apr. 26, 2023, the disclosure of which is hereby incorporated by reference in its entirety, including all figures, tables, and drawings.

BACKGROUND

Water is the most destructive agent of concrete structures and components. Water contributes to chemical reactions as a reagent and can act as a solvent, or a reacting medium, making transport of solutes and reactions possible. These harmful reactions are drastically reduced or in some cases are not possible without water. For that reason, dry concrete has a much longer lifespan than water saturated concrete. With challenges facing the nation for upgrading the nation's infrastructure, there is an urgent need for methodology that can be used to assess the permeability of concrete elements of existing structures, that is not invasive, that can provide information in a very short time (e.g., in certain cases 10 to 20 minutes), and that is easy for field application.

BRIEF SUMMARY

Embodiments of the subject invention provide novel systems and methods to simulate concrete elements being placed under pressures equivalent to several hundred feet of ocean water and provide information useful to assess relative durability of concrete without coring or other destructive actions. The quality of concrete can be assessed by measuring an amount of (or the pressure drop of) water or other liquid to ingress through the concrete surface under high pressure over time.

Embodiments of the subject invention provide a novel and unique rapid assessment of quality of existing concrete. Embodiments provide uniquely advantages systems and methods for assessing long term durability of existing concrete elements such as those used in midrise buildings, parking garages, bridge decks, and the like.

In an embodiment, a system for in situ rapid testing for assessing quality of a concrete test specimen at a test area on an outer surface thereof can comprise: a pressure fitting configured and adapted to deliver a test liquid at a sustained and measurable pressure to the test area; a gasket configured and adapted to seal the pressure fitting to the outer surface of the concrete test specimen around the test area; a support structure configured and adapted to secure the pressure fitting with respect to the outer surface of the concrete test specimen and the gasket under one or more forces created by the sustained and measurable pressure of the test liquid; a pressure source configured and adapted to generate the sustained and measurable pressure of the test liquid; a plumbing structure configured and adapted to deliver the test liquid from the pressure source to the pressure fitting; a pressure measurement device configured and adapted to measure the sustained and measurable pressure of the test liquid, creating a series of pressure measurements over time; and a data acquisition module configured and adapted to record the series of pressure measurements over time. The pressure fitting can comprise a round pipe flange with a pipe flange sealing surface configured and adapted to compress the gasket against the outer surface of the concrete test specimen around the test area when acted upon by the support structure. The gasket can be configured and adapted to seal against the outer surface of the concrete test specimen around the test area when acted upon by the pressure fitting. The support structure can be configured and adapted to transfer a force between the pressure fitting and the concrete test specimen, causing the pressure fitting to compress the gasket against the outer surface of the concrete test specimen around the test area. The round pipe flange can have an outer flange diameter; the outer flange diameter can be measured in a first plane parallel to the outer surface at the center of the test area when the pipe flange is compressing the gasket; the support structure can be contained within a support footprint diameter measurable in the first plane; and/or the support footprint diameter can be less than 5 times the outer flange diameter (e.g., the support footprint diameter can be less than 2 times the outer flange diameter, less than 1.5 times the outer flange diameter, or equal to or less than the outer flange diameter). The support footprint diameter can be equal to or less than the outer flange diameter, and the support structure can contact the concrete test specimen only outside of the test area. The pipe flange sealing surface can be a flat (or substantially flat) surface. The pipe flange sealing surface can alternatively be a convex surface or a concave surface. The support structure can comprise one or more fasteners mounted directly in or on the outer surface of the concrete test specimen. The support structure can comprise one or more fasteners mounted directly in or on a surface other than the outer surface of the concrete test specimen. The support structure can comprise a clamping member configured and adapted to apply force to the pressure fitting without penetrating or mounting into the concrete test specimen.

In another embodiment, a method for in situ rapid testing for assessing quality of a concrete test specimen at a test area on an outer surface thereof can comprise: providing a sustained static pressure of a test fluid to the test area on the outer surface of the concrete test specimen; measuring the static pressure of the test fluid over a test period to create a multiplicity of test measurements; recording the multiplicity of test measurements to create a test data set; analyzing the test data set to determine a test result; and reporting the test result. The step of analyzing the test data set can comprise sub steps of: creating a validation standard; and comparing the test data set against the validation standard to determine the test result. The sub step of creating a validation standard can comprise testing one or more concrete samples of known quality (e.g., using a testing method as described herein) to produce a validation data set. The validation standard can comprise either a threshold value, a slope of a line, or both, derived from the validation data set. The method can further comprise: identifying the concrete test specimen and the test area on an existing concrete structure; attaching a system for in situ rapid testing to the concrete test specimen around the test area; and using the system for in situ rapid testing to provide the sustained static pressure of the test fluid to the test area.

DETAILED DESCRIPTION

Embodiments of the subject invention provide novel systems and methods that can simulate concrete elements being placed under pressure equivalent to several hundred feet of ocean water and provide information to assess relative durability of concrete without coring or destructive action. The quality of concrete can be assessed by its ability to resist the ingression of water or any other liquid passing through the concrete surface under a specified pressure high pressure for a measured time (e.g., in certain embodiments, 20 minutes or less, alternatively 30 minutes or less, 15 minutes or less, 10 minutes or less, 5 minutes or less, 3 minutes or less, or about 2 minutes).

Embodiments provide new systems and methods for rapid assessment of existing concrete elements. The novel non-destructive testing systems and methods are based on applying liquid at relatively high pressure to a surface of a concrete element that it is being evaluated for long term durability according to its resistance against moisture ingress. Submerging the element of concrete under one foot of water generates about 0.433 pounds per square inch (psi) of pressure on the surface. As an example, exerting 200 psi pressure on the surface of concrete element under evaluation is equivalent to submerging that concrete under about 460 feet of water. The better the quality of concrete, the less the amount of water or any liquid that can penetrate through the concrete surface under a given pressure. The amount of water or any liquid penetrating through the surface of a concrete element, under evaluation and under pressure, can be measured using several methods, including the studying the pressure drop versus time of water or any liquid ingress through the surface.

Figure 1:
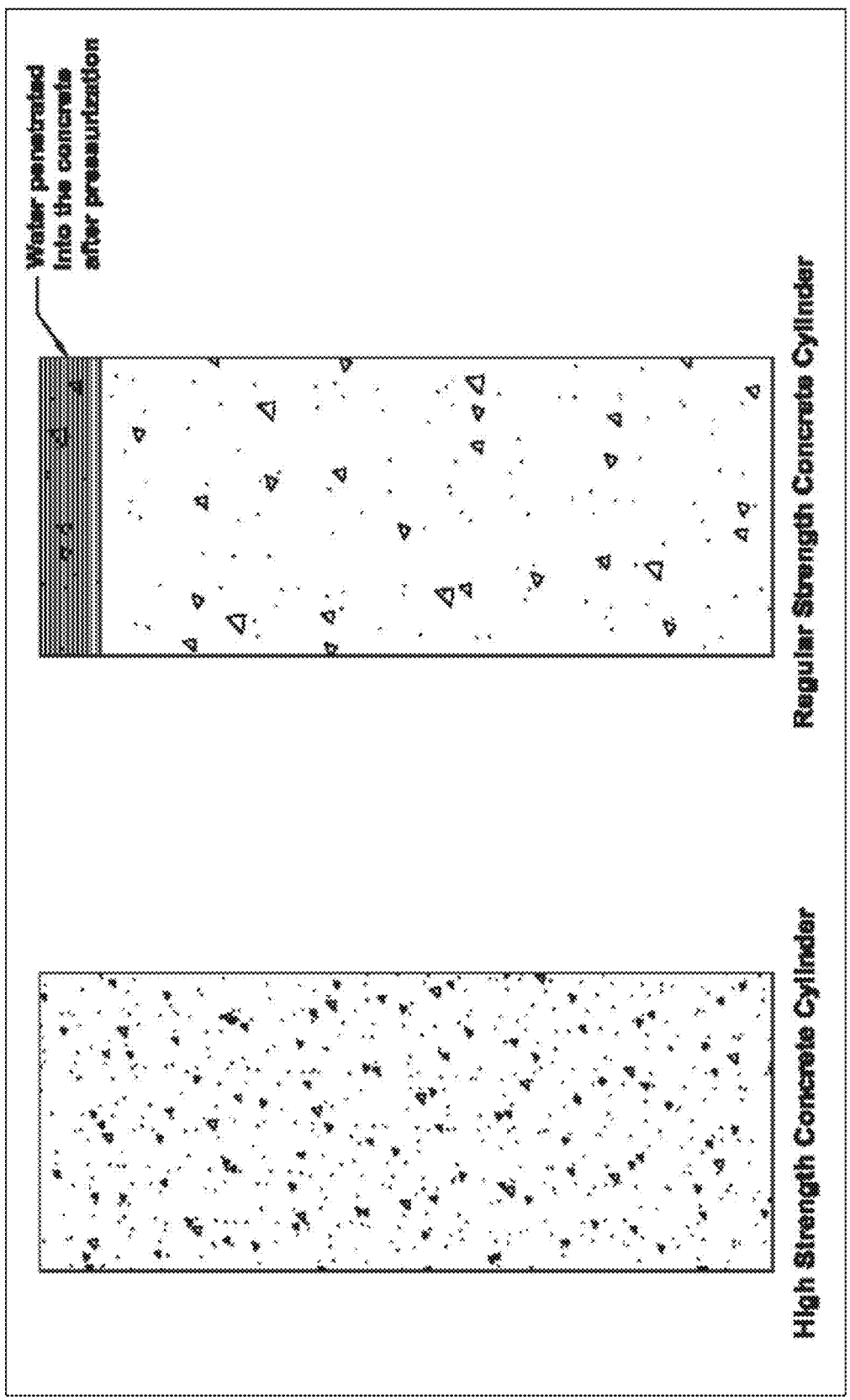
FIG. 1 shows two concrete elements evaluated for durability after testing according to an embodiment of the subject invention.

FIG. 1 shows two concrete elements evaluated for durability after testing according to an embodiment of the subject invention. Both concrete elements were subjected to about 200 PSI water pressure for a period of about 30 minutes. On the left, a first concrete element is a very high-quality concrete, called Ultra High-Performance Concrete (UHPC). On the right, a second concrete element represents types of concrete that are broadly used in construction of modern infrastructure. The concrete element on right shows a ring of water that is indicative of water penetrating through the top surface, while the concrete element on the left demonstrates that by using higher quality of concrete such as UHPC, the element has been made more durable in terms of preventing ingress of moisture through the concrete. Such ingress of moisture, especially salt water, is an important cause of corrosion in many existing infrastructures.

Figure 2:
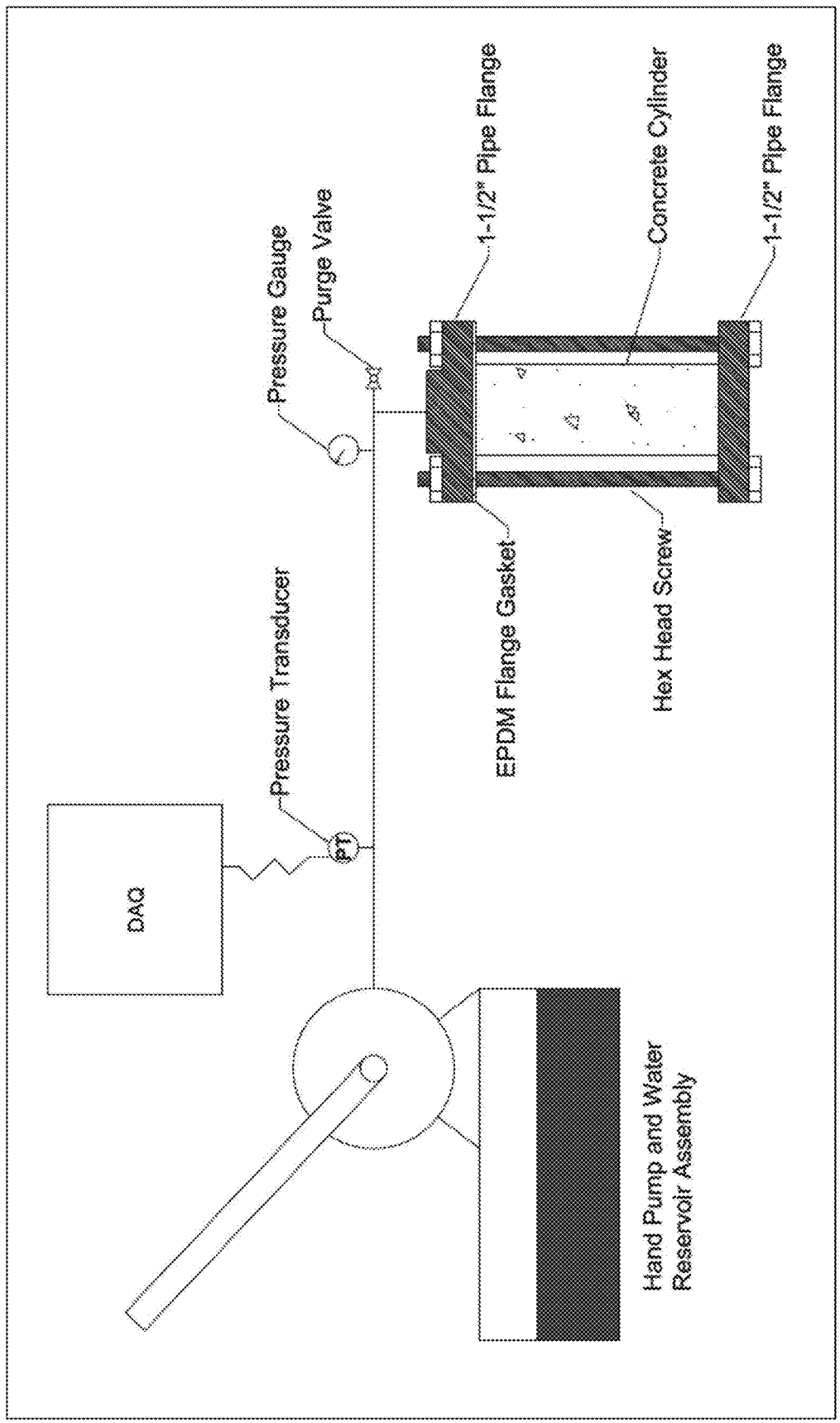
FIG. 2 shows a schematic diagram of a concrete cylinder testing configuration according to an embodiment of the subject invention.

FIG. 2 shows a schematic diagram of a concrete cylinder testing configuration according to an embodiment of the subject invention.

Figure 3:
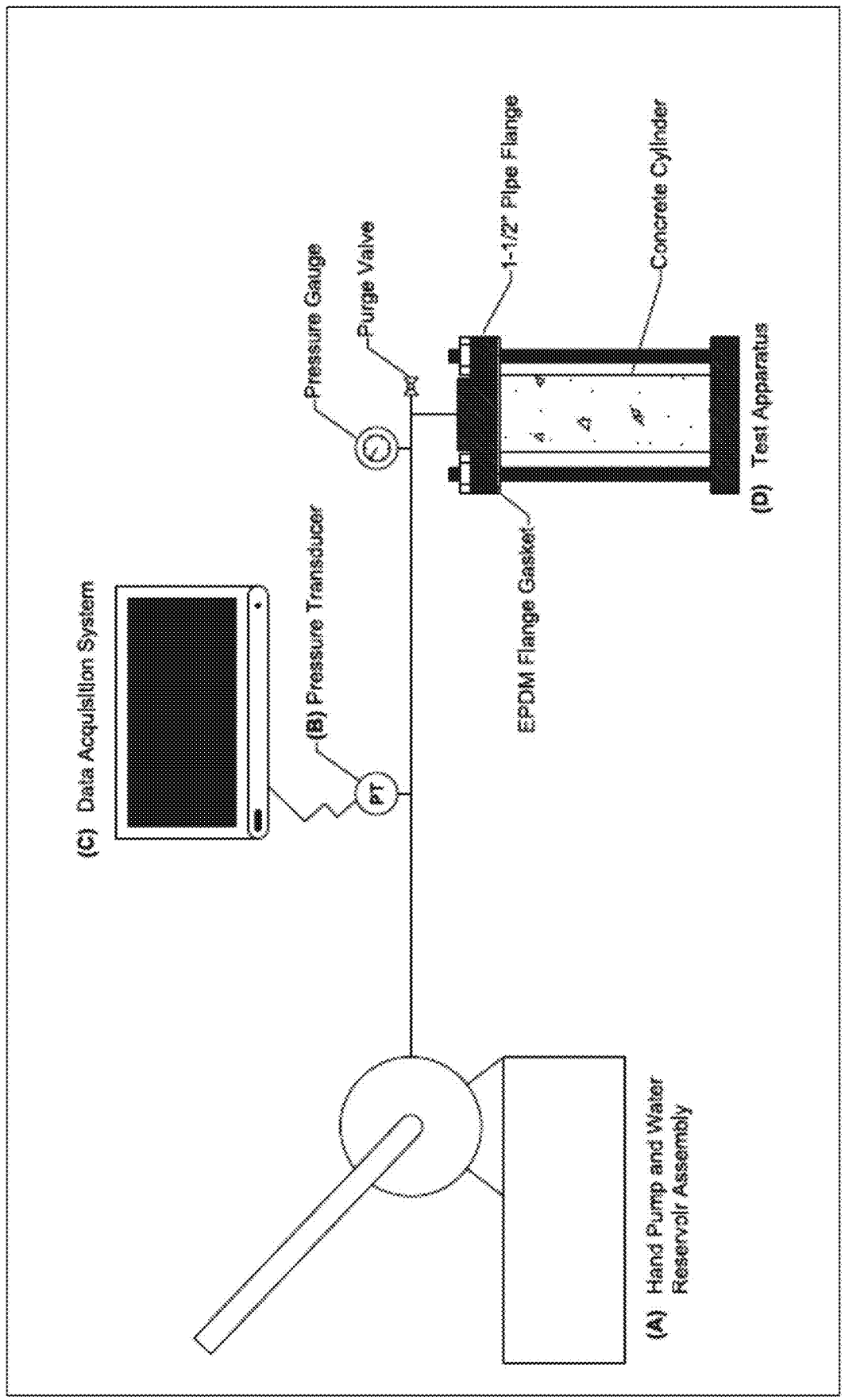
FIG. 3 shows a photograph of a concrete cylinder testing configuration according to an embodiment of the subject invention.

FIG. 3 shows a photograph of a concrete cylinder testing configuration according to an embodiment of the subject invention.

Figure 4:
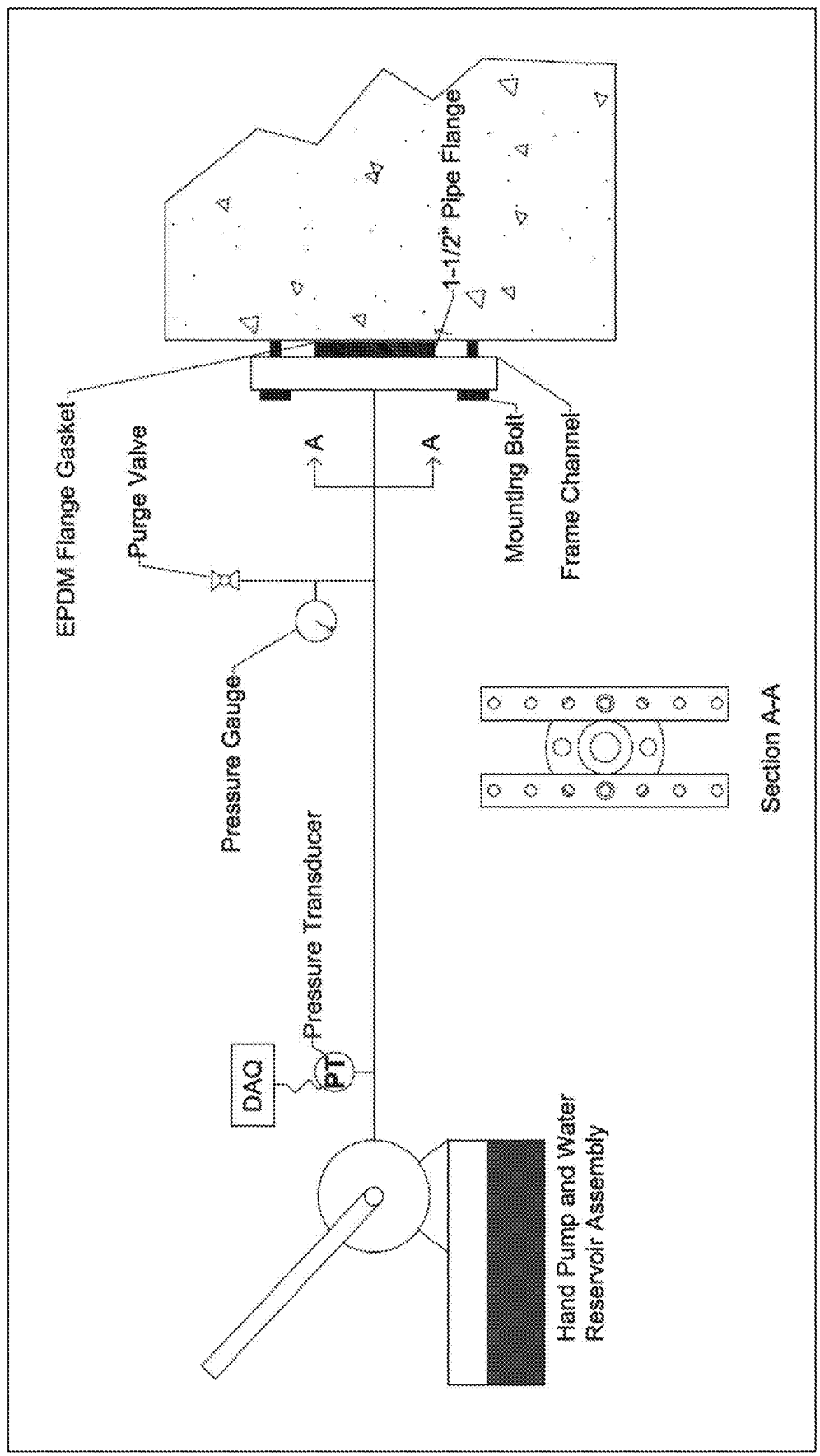
FIG. 4 shows a schematic diagram of a concrete wall or floor testing configuration according to an embodiment of the subject invention.

FIG. 4 shows a schematic diagram of a concrete wall or floor testing configuration according to an embodiment of the subject invention. In this embodiment the system can provide a concrete wall or floor (e.g., including a piling or support beam) testing configuration where two steel 1⅝" wide strut channels are used to secure the pressure pipe flange and the EPDM gasket to the concrete surface (e.g., in application to an existing structure comprising concrete or to a designated test specimen created with new construction, or to a concrete test specimen created at a different date and time.) In this embodiment each strut channel is secured to the concrete surface with two concrete anchor bolts. It is contemplated within the scope of the subject invention that the EPDM gasket can be provided with or replace by other effective gasket elements, including but not limited to gaskets of other materials, gaskets of various geometric configurations as known in the art or as may be later invented or developed, and gasket elements that are formed or provided as part of the pressure pipe flange, concrete test specimen, or both. It is contemplated within the scope of the subject invention that mounting hardware or structures and other interfacing features useful to the invention (e.g., bolts, nuts, other fasteners, pipe flanges, pipe fittings, support bars, frames, or brackets) can be provided as commercial off the shelf, modified, customized, or specially designed and fabricated purpose built components, parts, assemblies, or systems.

Figure 5:
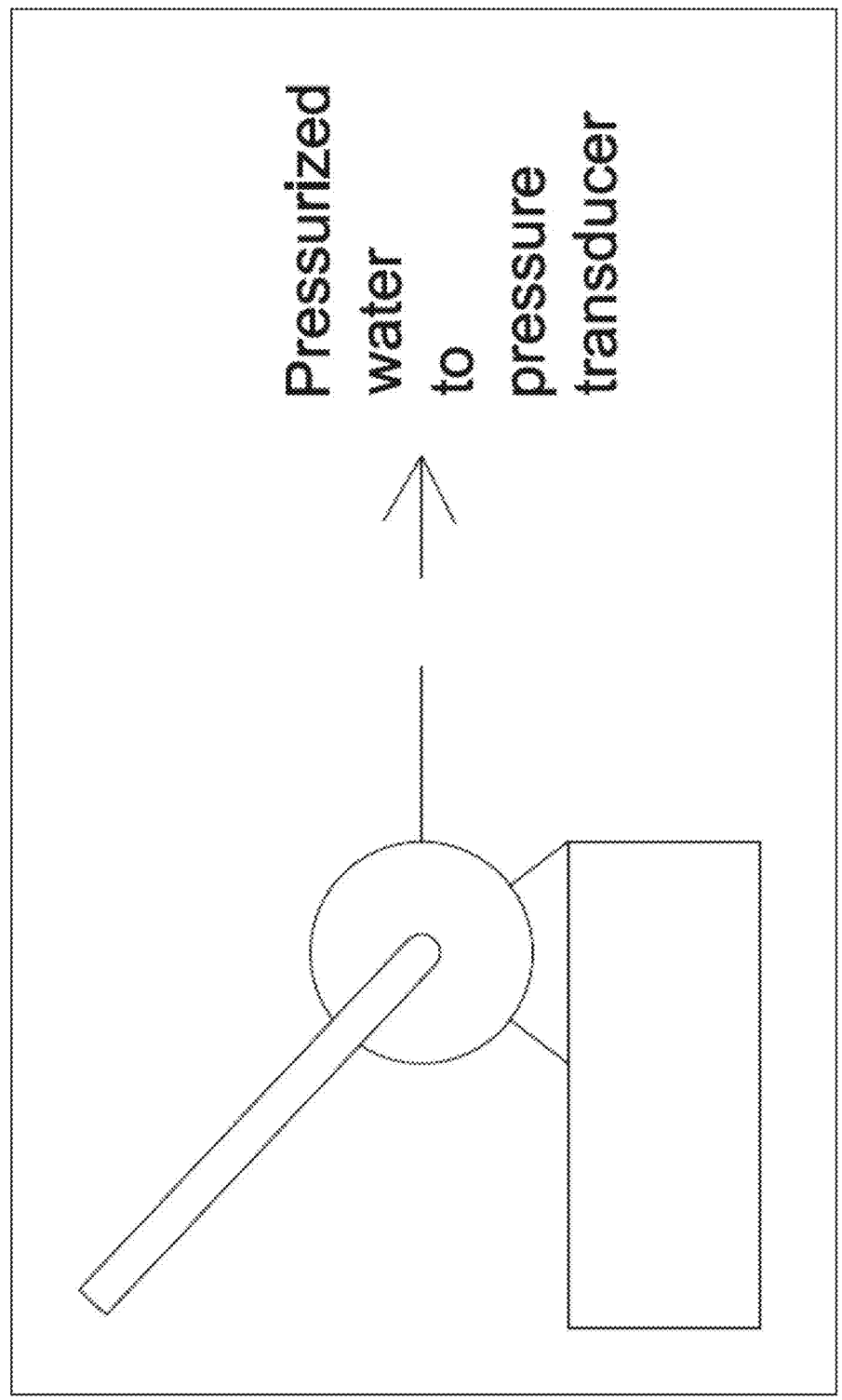
FIG. 5 shows a hydraulic test pump used in Example 1 according to an embodiment of the subject invention.

FIG. 5 shows a hydraulic test pump used in Example 1 according to an embodiment of the subject invention.

Figure 6:
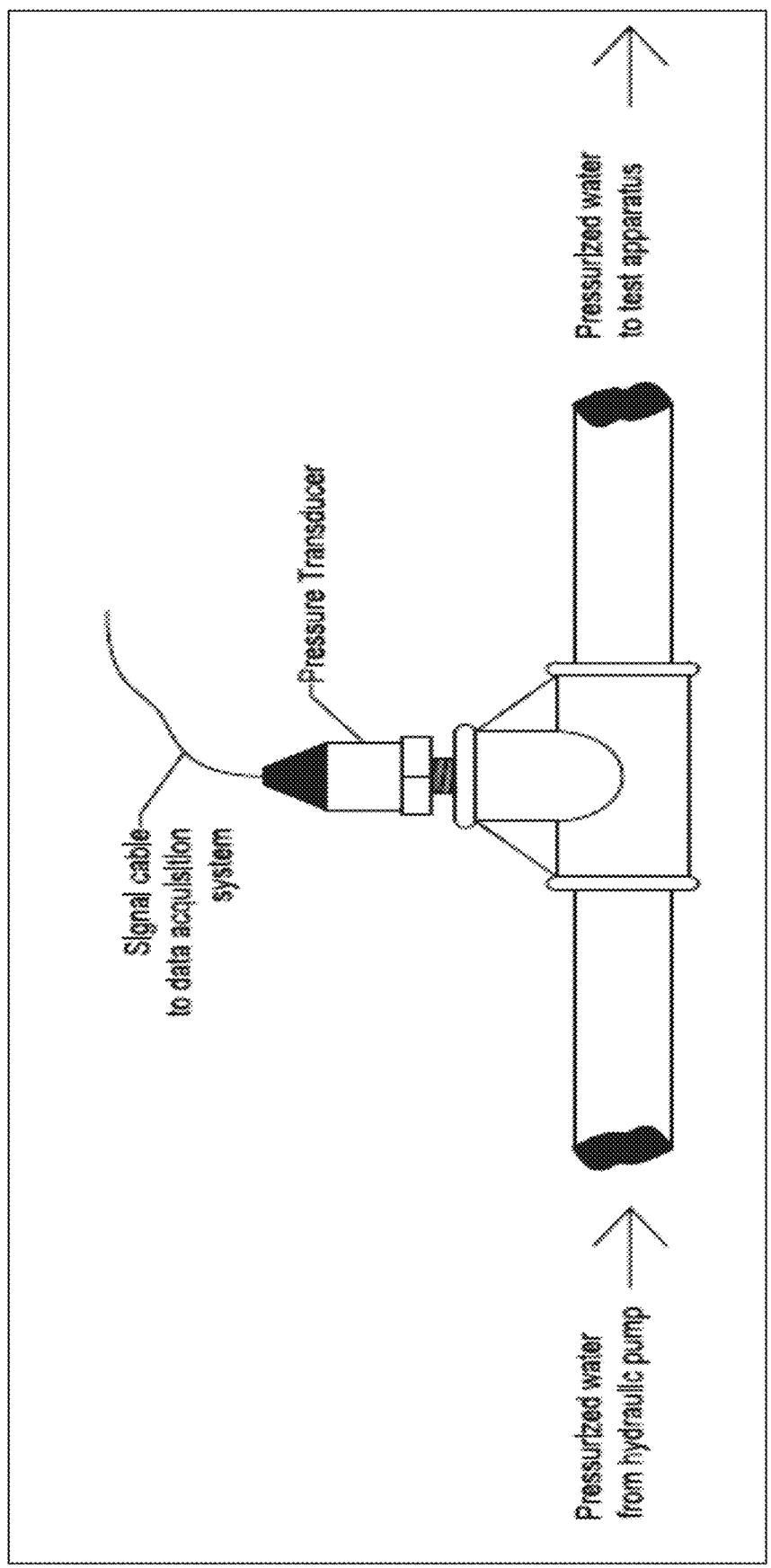
FIG. 6 shows a pressure transducer used in Example 1 according to an embodiment of the subject invention.

FIG. 6 shows a pressure transducer used in Example 1 according to an embodiment of the subject invention.

Figure 7:
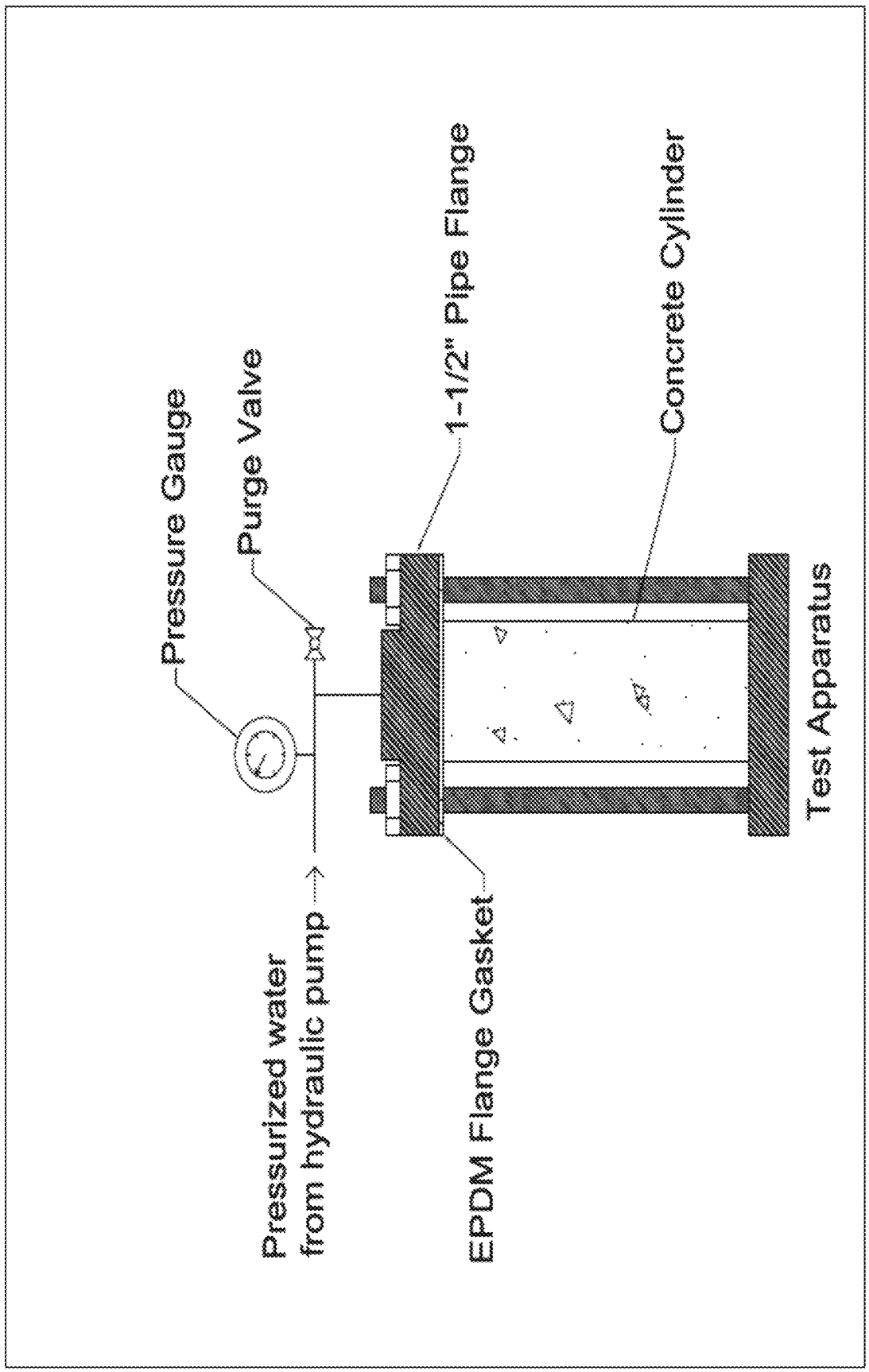
FIG. 7 shows a photograph of an apparatus for cylindrical used in Example 1 for testing according to an embodiment of the subject invention.

FIG. 7 shows a photograph of an apparatus for cylindrical used in Example 1 for testing according to an embodiment of the subject invention.

Figure 8:
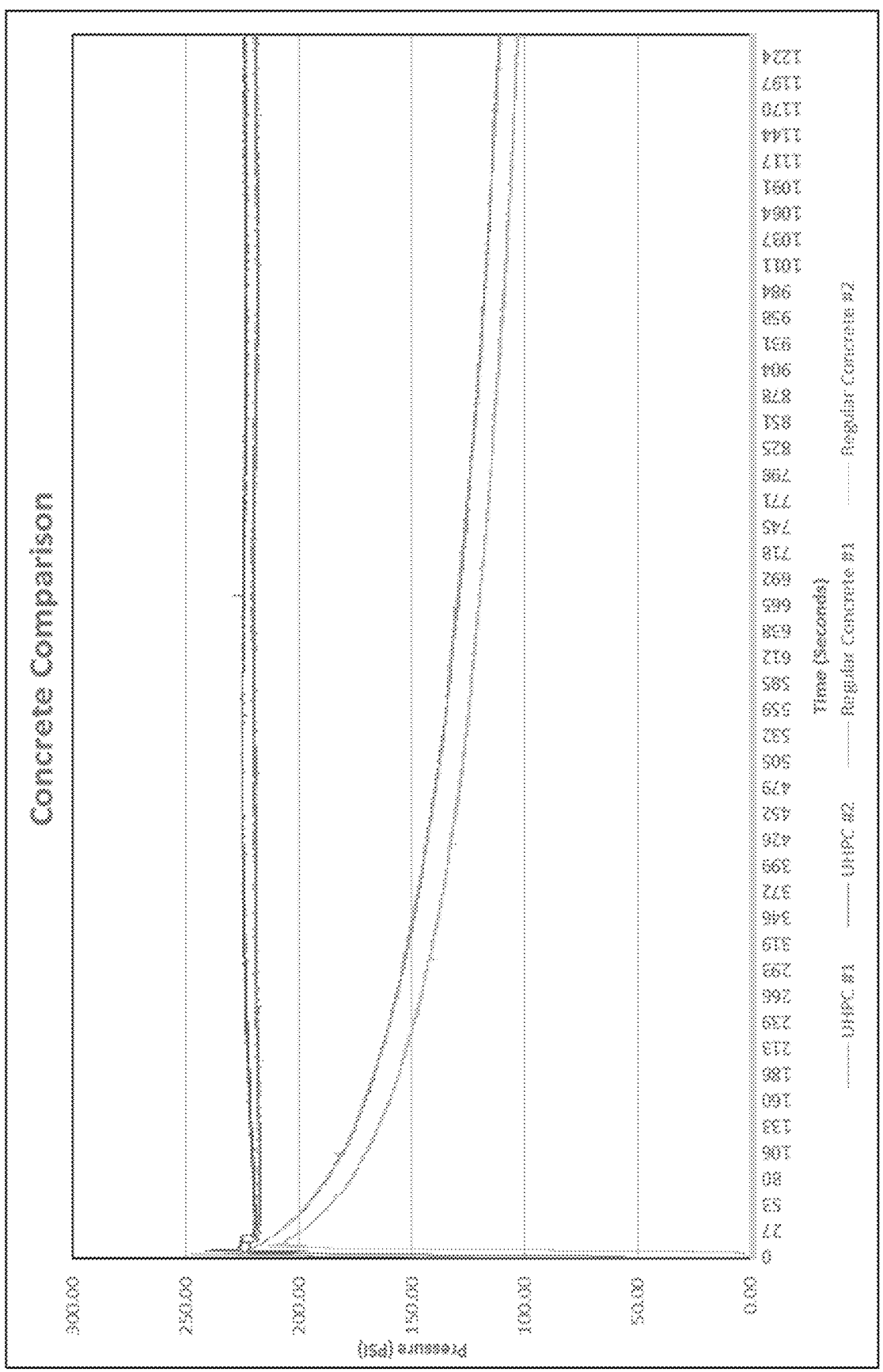
FIG. 8 shows combined testing results from Example 1 including pressure over time for two UHPC samples and two regular concrete samples according to an embodiment of the subject invention.

FIG. 8 shows combined testing results from Example 1 including pressure over time for two UHPC samples and two regular concrete samples according to an embodiment of the subject invention.

Figure 9:
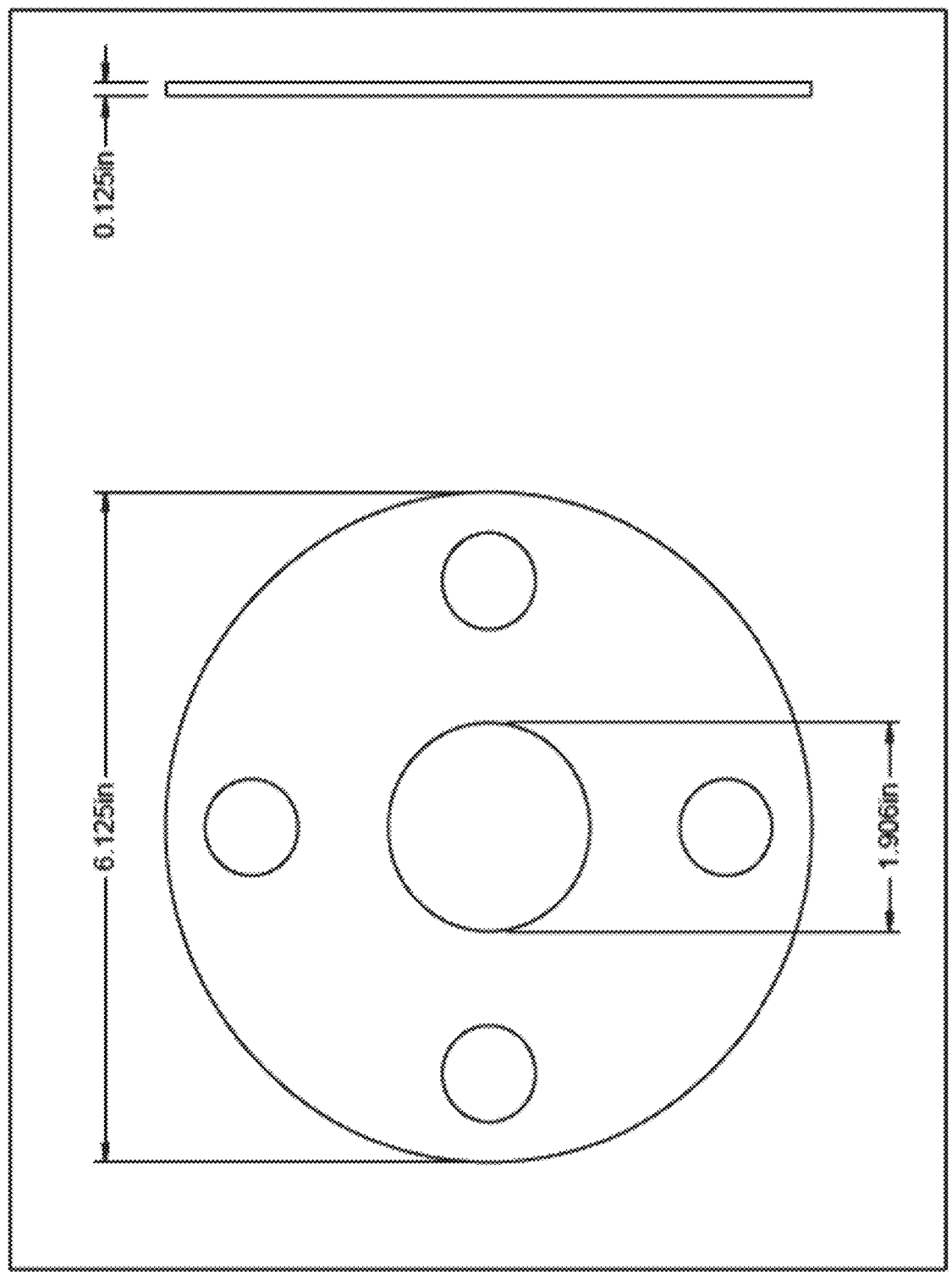
FIGS. 9-20 illustrate commercial off the shelf components utilized according to an embodiment of the subject invention (see also Example 1), including an EPDM gasket in FIG. 9, a pressure gauge in FIG. 10, a high pressure brass ball valve in FIG. 11, a high pressure steel pipe fitting in FIG. 12, ⅛" NPT thick wall welded steel pipe nipple in FIG. 13, 1½" NPT thick wall welded steel pipe nipple in FIG. 14, a medium pressure iron pipe fitting in FIG. 15, a medium pressure steel flange in FIG. 16, a thick wall steel seamless pipe nipple in FIG. 17, a low pressure pipe fitting in FIG. 18, an extreme pressure water hose in FIG. 19, and a low pressure steel unthreaded pipe flange in FIG. 20.
Figure 10:
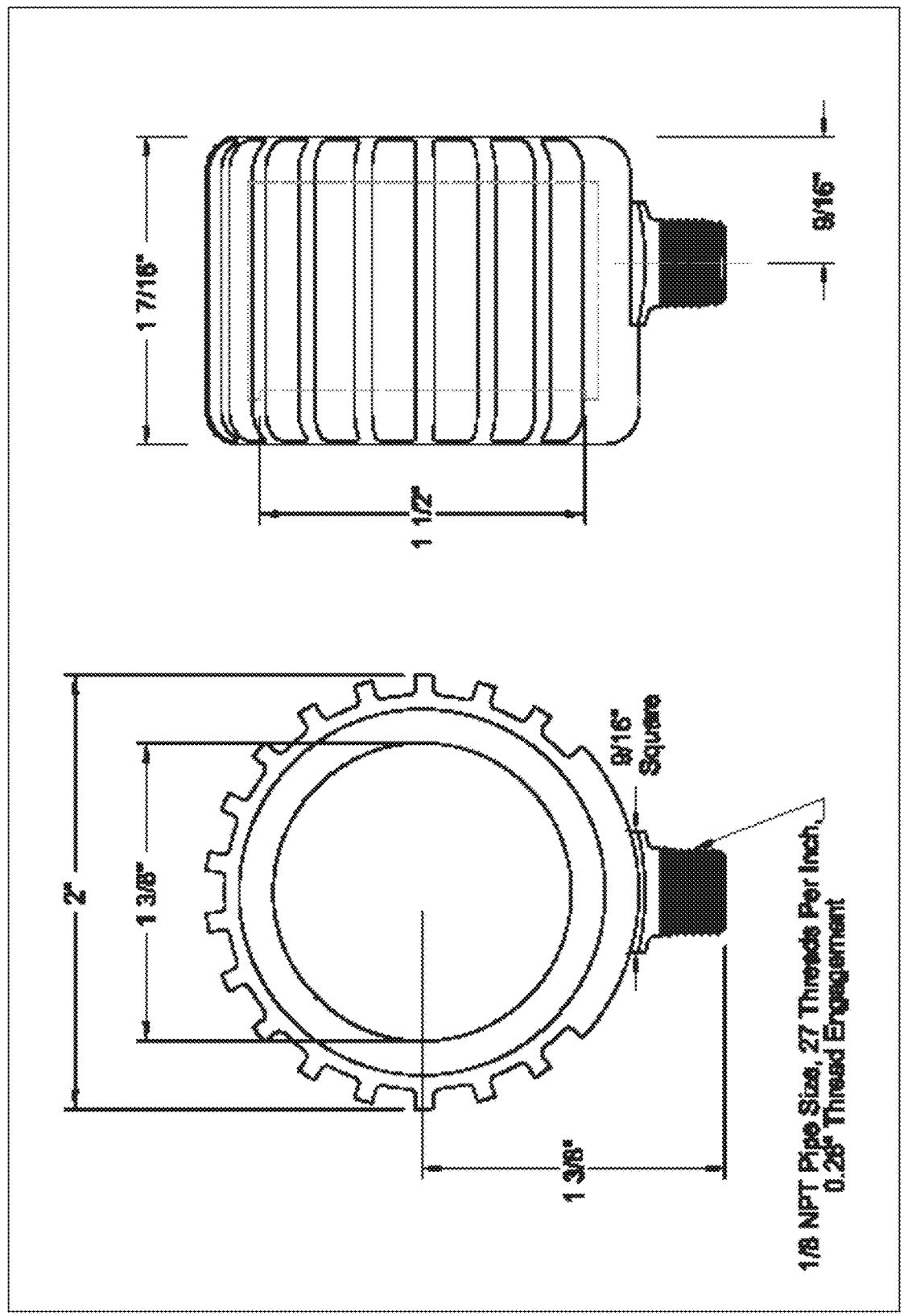
Figure 11:
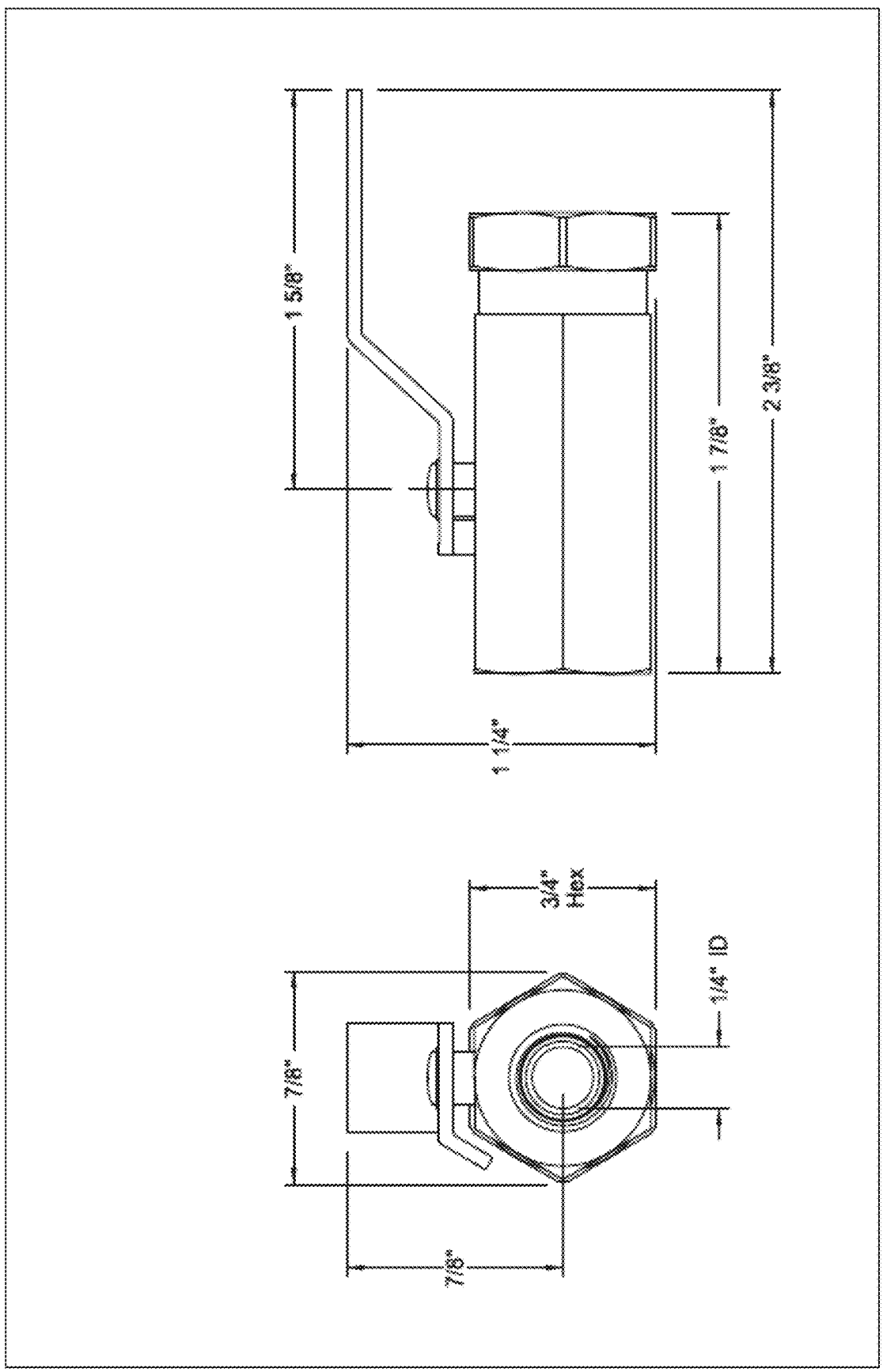
Figure 12:
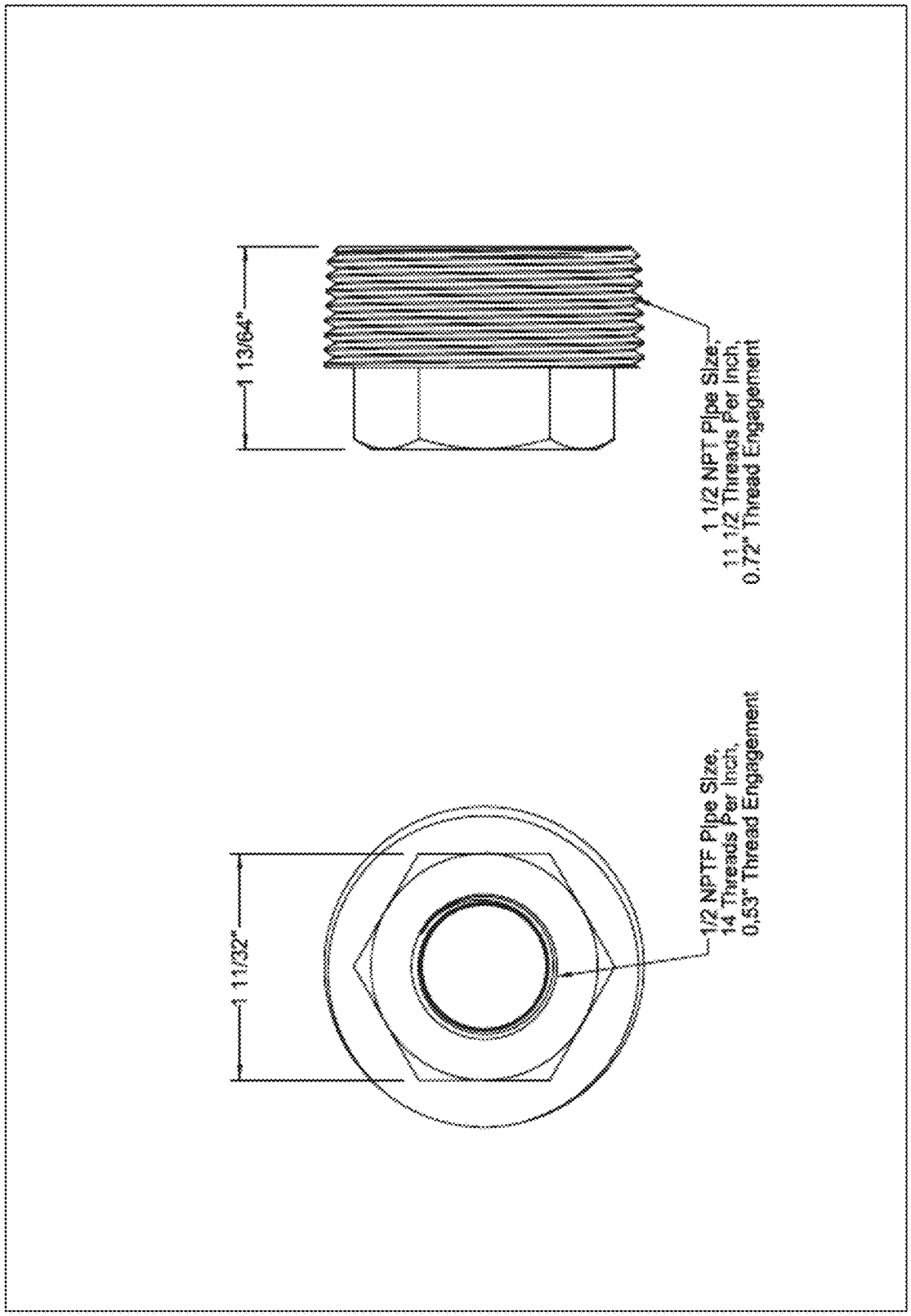
Figure 13:
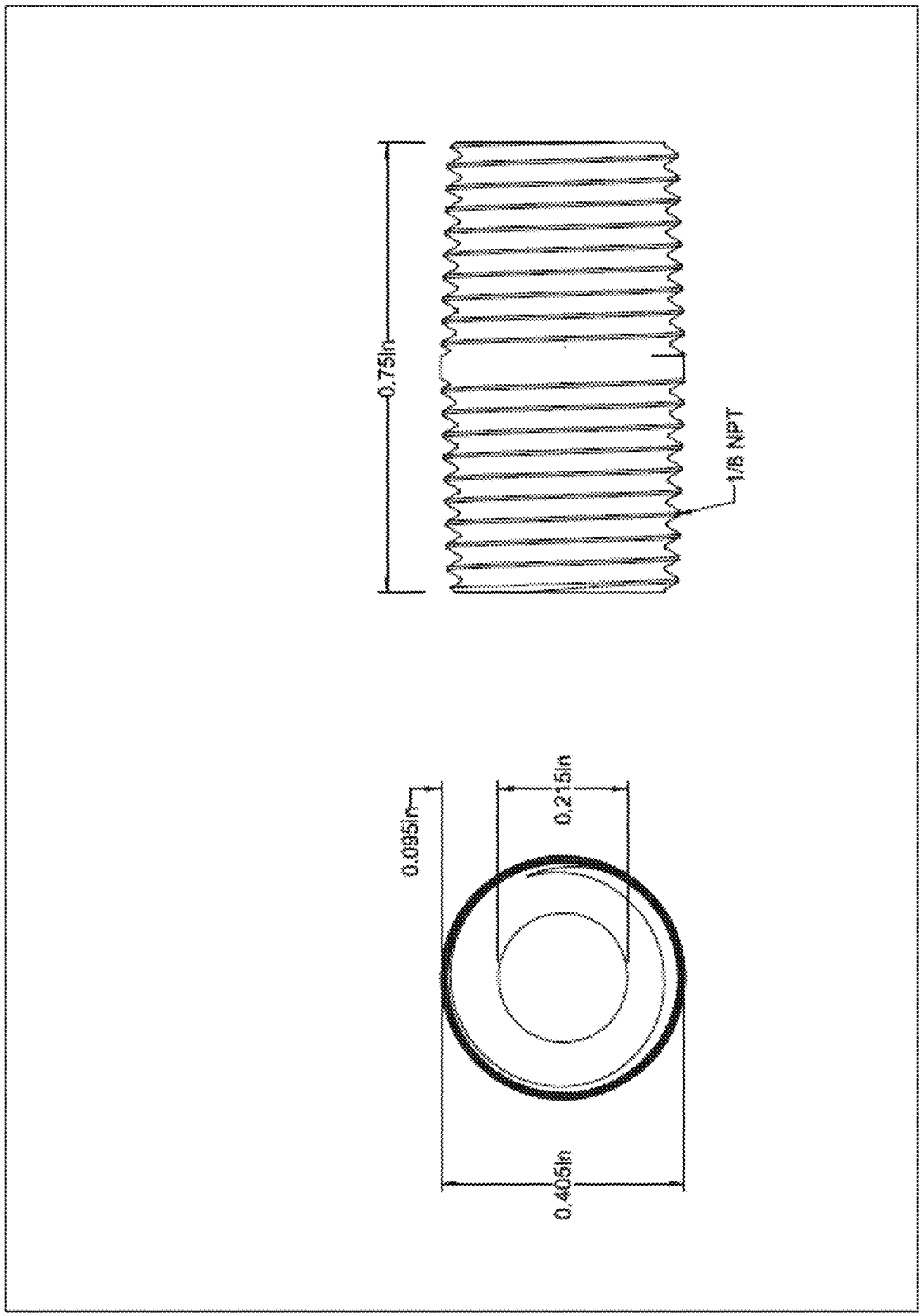
Figure 14:
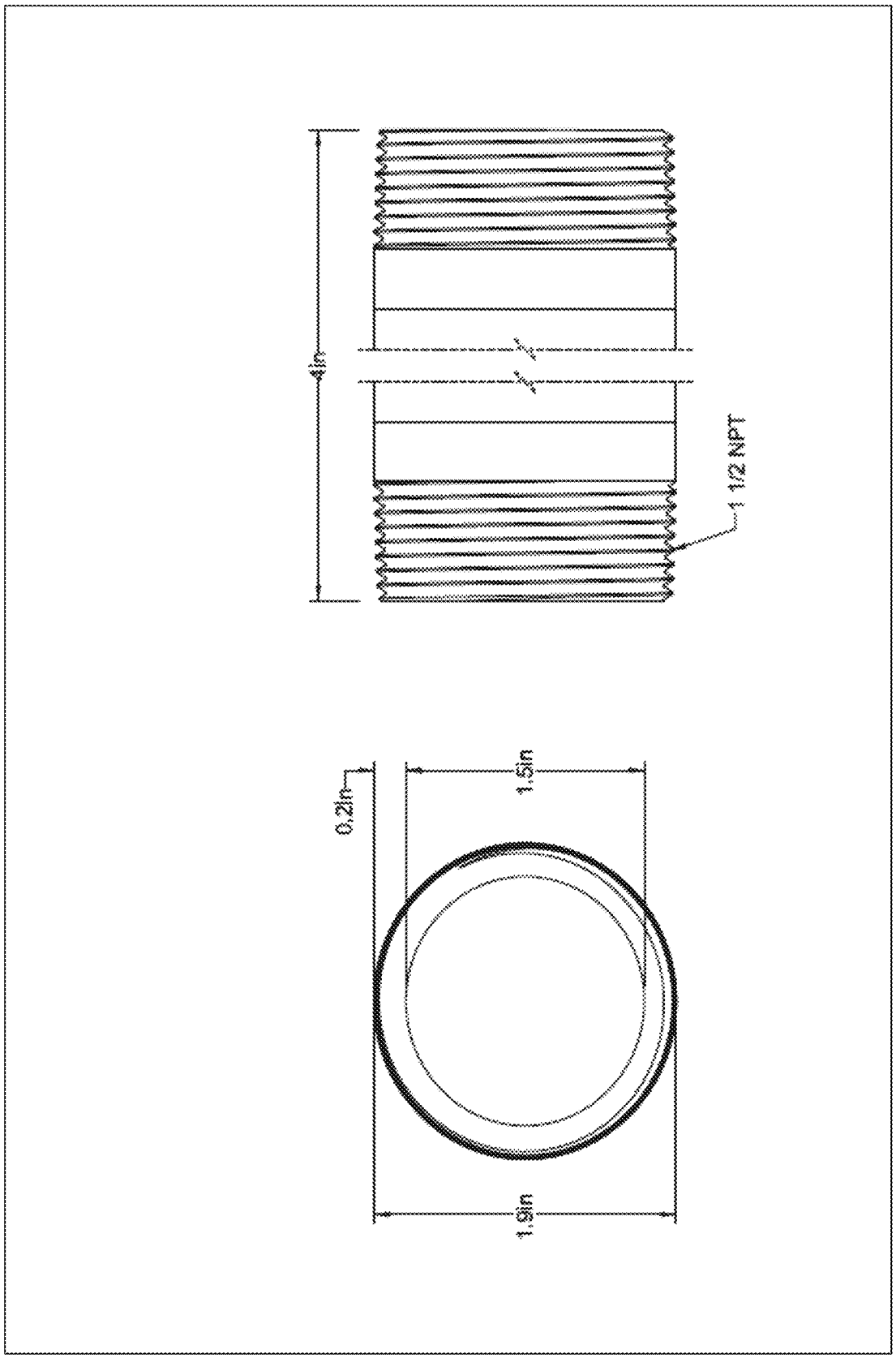
Figure 15:
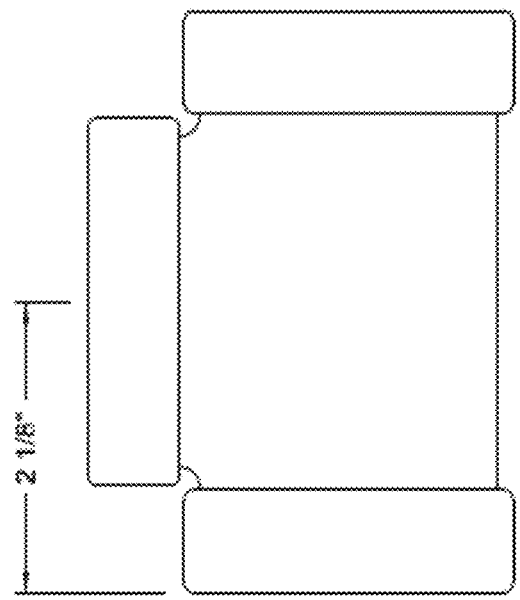
Figure 15:
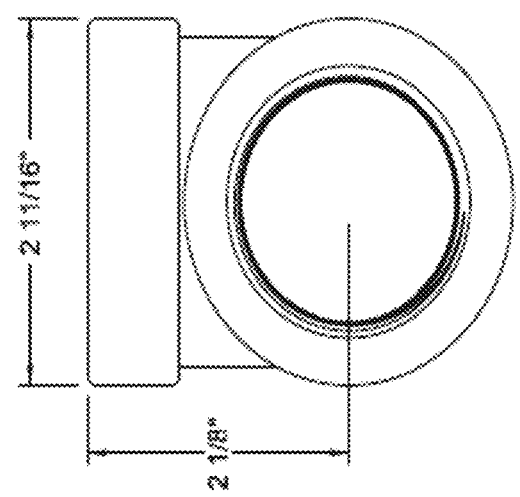
Figure 16:
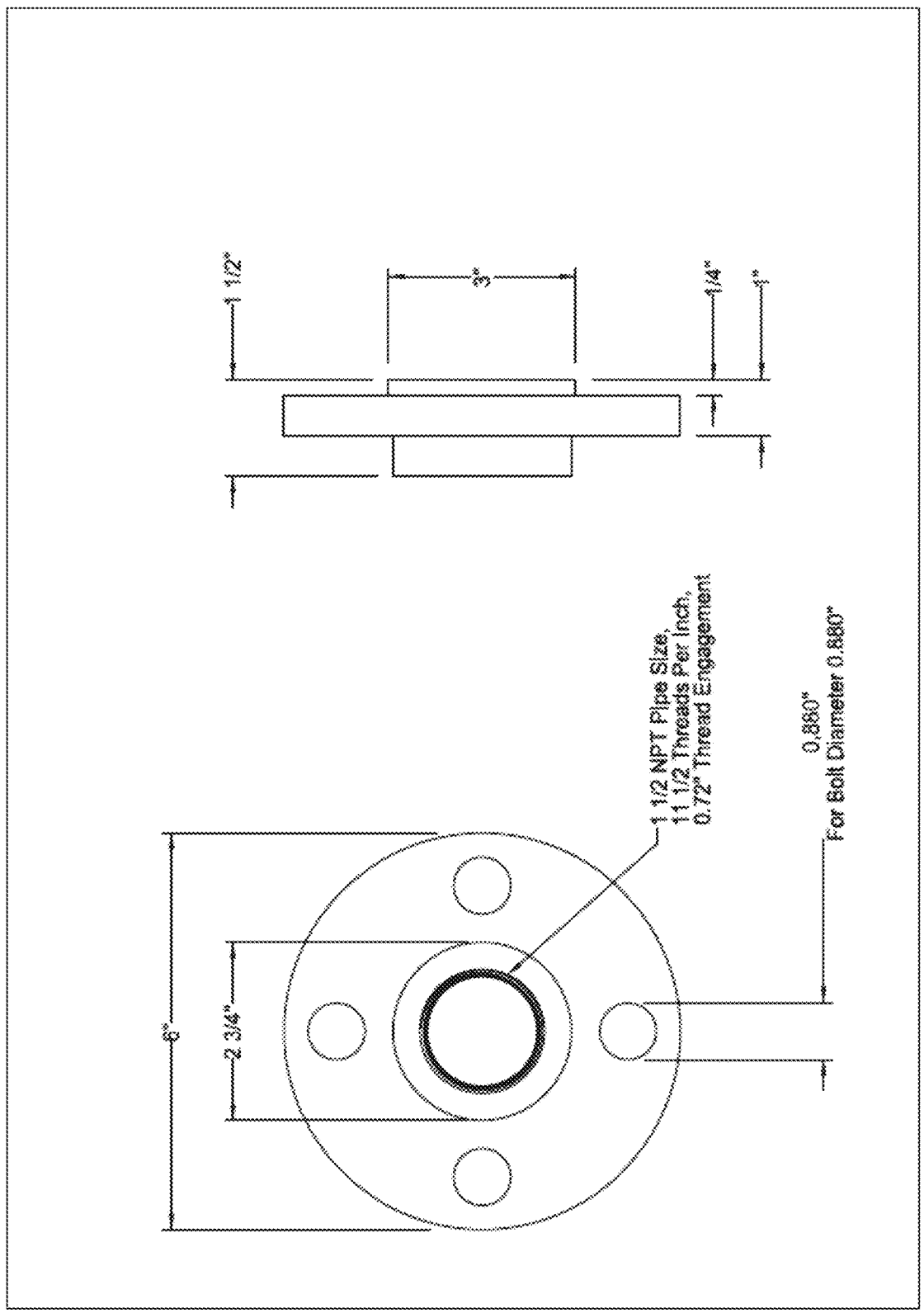
Figure 17:
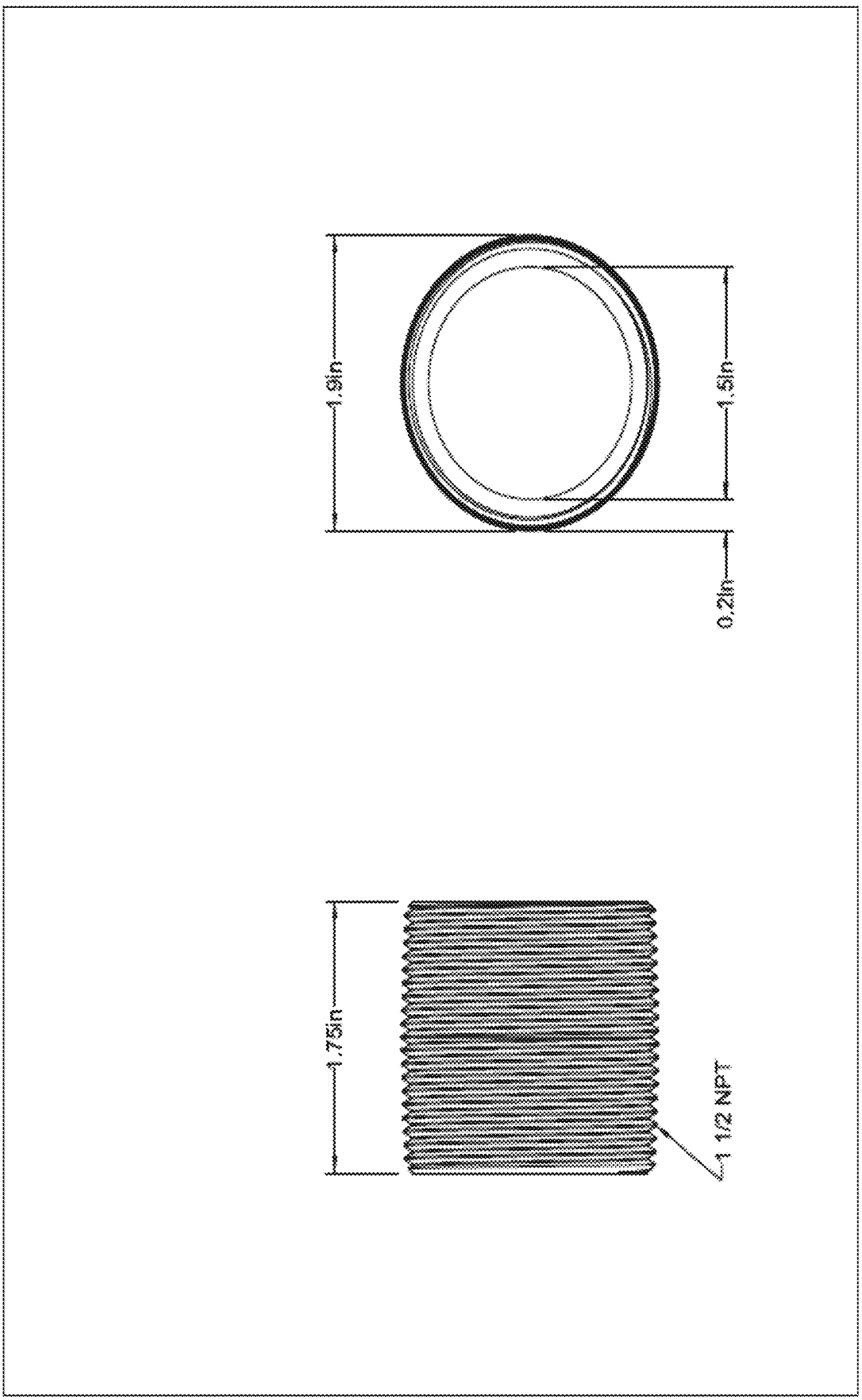
Figure 18:
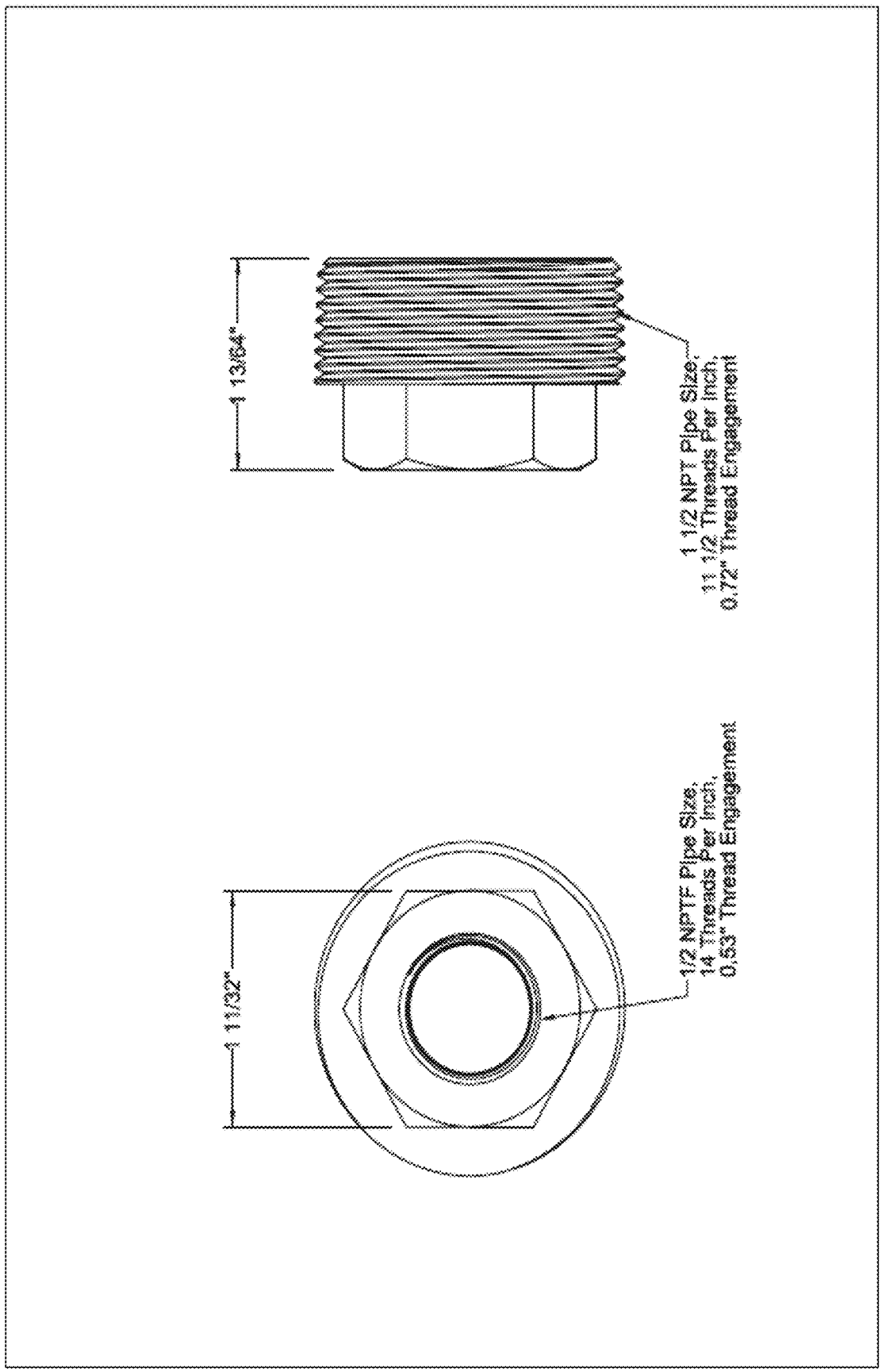
Figure 19:
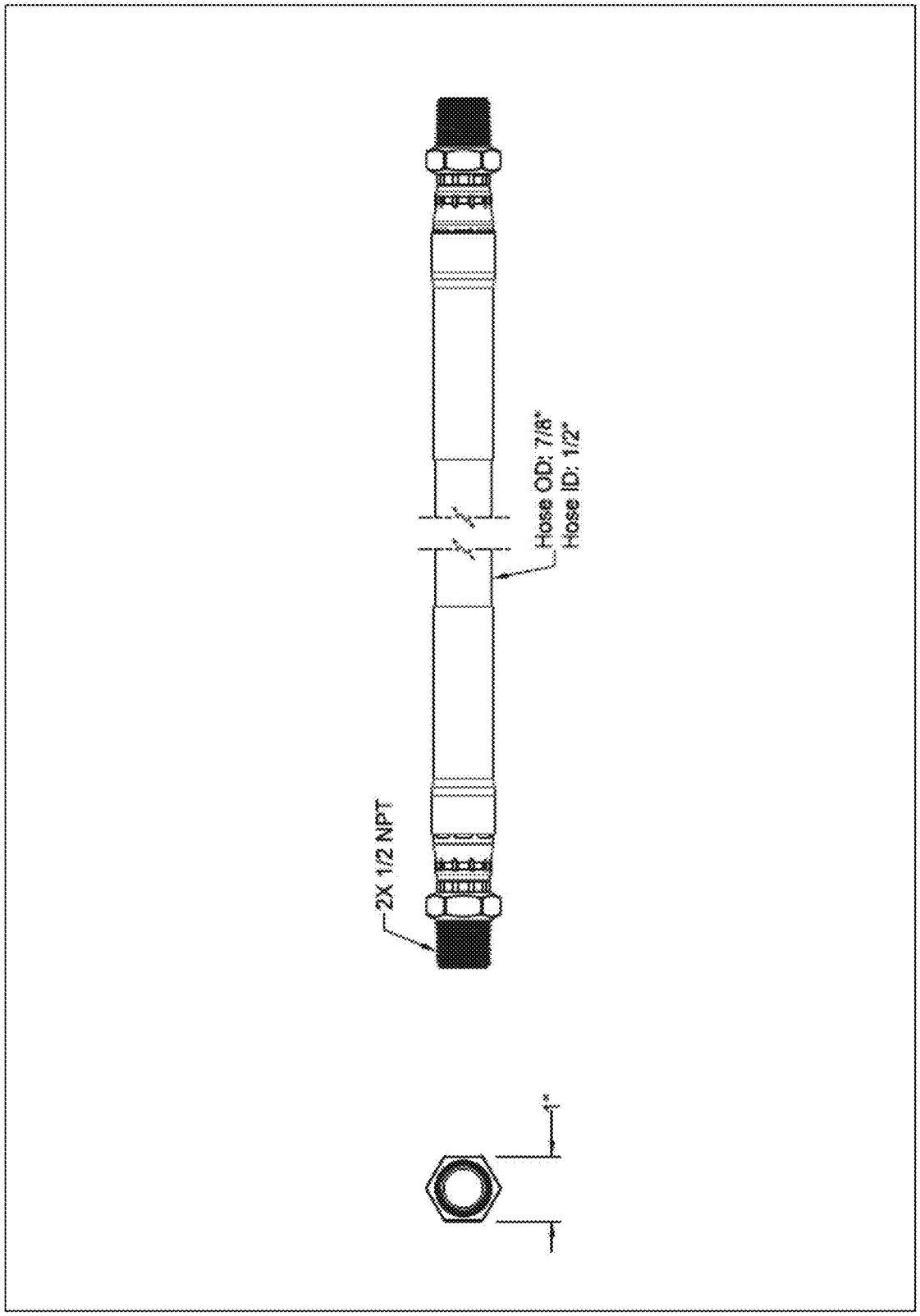
Figure 20:
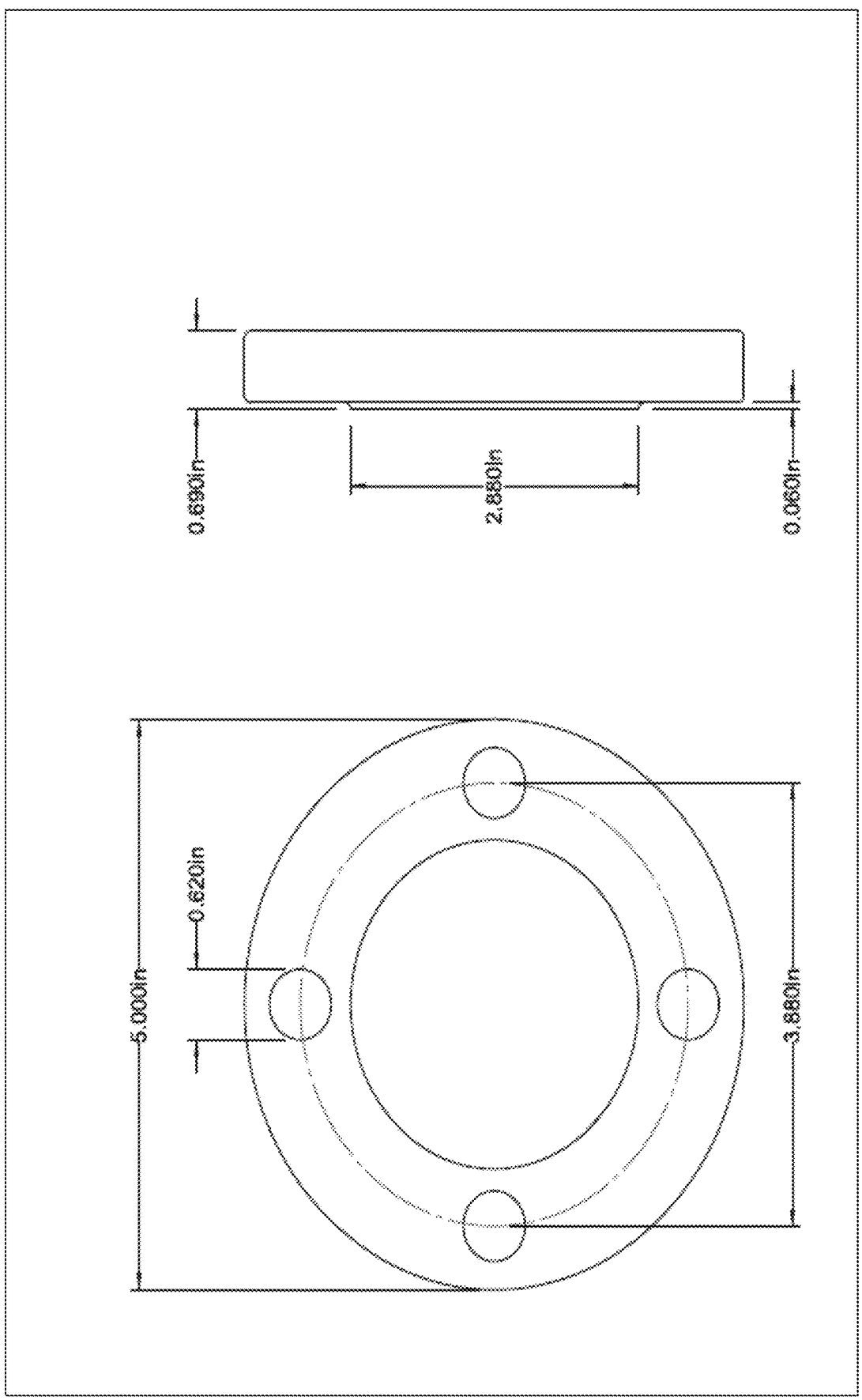

FIGS. 9-20 illustrate commercial off the shelf components utilized in Example 1 according to an embodiment of the subject invention, including an EPDM gasket in FIG. 9, a pressure gauge in FIG. 10, a high pressure brass ball valve in FIG. 11, a high pressure steel pipe fitting in FIG. 12, ⅛" NPT thick wall welded steel pipe nipple in FIG. 13, 1½" NPT thick wall welded steel pipe nipple in FIG. 14, a medium pressure iron pipe fitting in FIG. 15, a medium pressure steel flange in FIG. 16, a thick wall steel seamless pipe nipple in FIG. 17, a low pressure pipe fitting in FIG. 18, an extreme pressure water hose in FIG. 19, and a low pressure steel unthreaded pipe flange in FIG. 20.

When ranges are used herein, combinations and subcombinations of ranges (e.g., subranges within the disclosed range) and specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Example 1—Non-Destructive Testing Apparatus and Method

The following is a description of the setup used in a non-destructive test according to an embodiment of the subject invention. FIG. 2 and FIG. 3 show the basic components of a system according to one embodiment in a cylinder testing configuration. Components visible in FIG. 3 include a hand pump and water reservoir assembly (8A) that provides pressurized water (or any other fluid that can be pumped). The pressure of the pressurized fluid is measured by a pressure transducer (8B) and the pressure as well as the time are recorded by an Arduino® data acquisition module connected to a laptop computer (8C). The pressurized water is then delivered to the test apparatus (8D) where the pressure is measured with a pressure gauge and any trapped air is purged from the line before beginning the test.

FIG. 4 shows the system in a concrete wall or floor (including piling or support beam) testing configuration where two steel 1⅝" wide strut channels are used to secure the pressure pipe flange and the EPDM gasket to the concrete surface. As shown in inset detail Section A-A, each strut channel is secure to the concrete surface with two concrete anchor bolts in an exemplary but non-limiting embodiment.

Components included a hydraulic test pump, pressure transducer, and test apparatus (e.g., including pipe flanges, sealing gaskets, and hardware selected for a specific application.) Test procedures according to an embodiment of the subject invention were followed, and data including pressure drop over time were collected for each test sample.

The hydraulic test pump shown in FIG. 5 is a Rothenberger model RP 50-S (Rothenberger USA, Loves Park, Ill.). It has a maximum pressure of 860 psi with dual isolation valves and a pressure gauge with maximum pressure indicator. It is also equipped with an onboard test fluid reservoir which allows for use without the need to connect to a water hose.

The pressure transducer shown in FIG. 6 is an Omega Engineering model PX191-700GV5 with a 0-700 psi range (Omega Engineering Inc., Norwalk, CT). The pressure data is collected via an Arduino data acquisition module connected to a laptop computer.

FIG. 7 shows the test apparatus for the cylinder testing configuration that utilizes four long hex screw and nuts to sandwich the concrete cylinder between two 1½" steel pipe flanges. The top flange has a hole in the center where the pressurized water is applied to the top surface of the concrete cylinder. An EPDM flange gasket is used to seal the top of the cylinder and prevent the water from leaking out.

Once the system is attached to the concrete specimen to be tested and the reservoir is filled with the test fluid, the air is purged out of the system by opening the purge valve while pumping the hand pump. Once all the air is purged, the purge valve is closed and the data acquisition system is started. The system is pressurized to pressure between 200 to 250 psi. The isolation valve on the pump is closed in order to maintain the pressure on the specimen and a 20 minute timer is started. After 20 minutes the data acquisition system is stopped and the data is collected and analyzed.

The system was tested on concrete cylinder made from Ultra High Performance Concrete (UHPC) as well regular concrete. As can be seen from FIG. 8, the UHPC specimens had an average pressure drop of 19 psi after 20 minutes of testing. However, the regular concrete specimens had an average pressure drop of 125 psi after 20 minutes of testing.

FIG. 1 shows concrete specimens evaluated for durability using the setup described. Both concrete elements were subjected to about 200 PSI water pressure for a period of about 20 minutes. The left concrete specimen is a very high-quality concrete, called Ultra High-Performance Concrete (UHPC). The specimen on the right represents the type of concrete that are commonly used in construction of infrastructure. The concrete specimen on right shows a ring of water that is indicative of water penetrating through the top surface, while the specimen on the left shows no visual sign of water penetration. This is in good agreement with pressure results shown in FIG. 8 and demonstrates that higher quality of concrete such as UHPC, the concrete element becomes more durable in terms of preventing ingress of moisture through the concrete. Such ingress of moisture, especially salt water is the main cause of corrosion in many existing infrastructures. Non-destructive testing utilizing this system can evaluate a wide variety of concrete structures and specimens for long term durability by determining their respective resistance to moisture ingress.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A method for in situ rapid testing for assessing quality of a concrete test specimen at a test area on an outer surface thereof, the method comprising the following steps:
   providing a sustained static pressure of a test fluid to the test area on the outer surface of the concrete test specimen, the static pressure being an elevated pressure equivalent to submerging the concrete test specimen under a predetermined depth of water;
   measuring the static pressure of the test fluid over a test period to create a multiplicity of test measurements;
   recording the multiplicity of test measurements to create a test data set;
   analyzing the test data set to determine a test result; and
   reporting the test result.

2. The method according to claim 1, the step of analyzing the test data set comprising sub steps of:
   creating a validation standard; and comparing the test data set against the validation standard to determine the test result,
the sub step of creating a validation standard comprising testing one or more concrete samples of known quality to produce a validation data set, and
the validation standard comprising either a threshold value, a sloe of a line, or both, derived from the validation data set.

3. The method according to claim 1, further comprising the following steps:
identifying the concrete test specimen and the test area on an existing concrete structure;
attaching a system for in situ rapid testing to the concrete test specimen around the test area; and
using the system for in situ rapid testing to provide the sustained static pressure of the test fluid to the test area.

4. The method according to claim 1, the static pressure being at least 200 pounds per square inch (psi).

5. The method according to claim 1, the static pressure being in a range of from 200 pounds per square inch (psi) to 250 psi.

6. A method for in situ rapid testing for assessing quality of a concrete test specimen at a test area on an outer surface thereof, the method comprising the following steps:
providing a sustained static pressure of a test fluid to the test area on the outer surface of the concrete test specimen;
measuring the static pressure of the test fluid over a test period to create a multiplicity of test measurements;
recording the multiplicity of test measurements to create a test data set;
analyzing the test data set to determine a test result;
reporting the test result;
identifying the concrete test specimen and the test area on an existing concrete structure;
attaching a system for in situ rapid testing to the concrete test specimen around the test area; and
using the system for in situ rapid testing to provide the sustained static pressure of the test fluid to the test area,
the system for in situ rapid testing comprising:
a pressure fitting configured and adapted to deliver the test fluid at the sustained static pressure to the test area;
a gasket configured and adapted to seal the pressure fitting to the outer surface of the concrete test specimen around the test area;
a support structure configured and adapted to secure the pressure fitting with respect to the outer surface of the concrete test specimen and the gasket under one or more forces created by the sustained static pressure of the test fluid;
a pressure source configured and adapted to generate the sustained static pressure of the test fluid;
a plumbing structure configured and adapted to deliver the test fluid from the pressure source to the pressure fitting;
a pressure measurement device configured and adapted to measure the sustained static pressure of the test fluid, creating a series of pressure measurements over time; and
a data acquisition module configured and adapted to record the series of pressure measurements over time.

7. The method according to claim 6, the pressure fitting of the system for in situ rapid testing comprising a round pipe flange with a pipe flange sealing surface configured and adapted to compress the gasket against the outer surface of the concrete test specimen around the test area when acted upon by the support structure.

8. The method according to claim 7, the pipe flange sealing surface being a substantially flat surface.

9. The method according to claim 7, the pipe flange sealing surface being a convex or concave surface.

10. The method according to claim 6, the gasket of the system for in situ rapid testing being configured and adapted to seal against the outer surface of the concrete test specimen around the test area when acted upon by the pressure fitting.

11. The method according to claim 6, the support structure of the system for in situ rapid testing being configured and adapted to transfer a force between the pressure fitting and the concrete test specimen, causing the pressure fitting to compress the gasket against the outer surface of the concrete test specimen around the test area.

12. The method according to claim 6, the round pipe flange of the system for in situ rapid testing having an outer flange diameter,
the outer flange diameter being measured in a first plane parallel to the outer surface at a center of the test area when the pipe flange is compressing the gasket,
the support structure being contained within a support footprint diameter measurable in the first plane, and
the support footprint diameter being less than 5 times the outer flange diameter.

13. The method according to claim 12, the support footprint diameter being less than 2 times the outer flange diameter.

14. The method according to claim 12, the support footprint diameter being less than 1.5 times the outer flange diameter.

15. The method according to claim 12, the support footprint diameter being equal to or less than the outer flange diameter, and the support structure contacting the concrete test specimen only outside of the test area.

16. The method according to claim 6, the support structure comprising one or more fasteners mounted directly in or on the outer surface of the concrete test specimen.

17. The method according to claim 6, the support structure comprising one or more fasteners mounted directly in or on a surface other than the outer surface of the concrete test specimen.

18. The method according to claim 6, the support structure comprising a clamping member configured and adapted to apply force to the pressure fitting without penetrating or mounting into the concrete test specimen.

19. A method for in situ rapid testing for assessing quality of a concrete test specimen at a test area on an outer surface thereof, the method comprising the following steps:
providing a sustained static pressure of a test fluid to the test area on the outer surface of the concrete test specimen, the static pressure being an elevated pressure equivalent to submerging the concrete test specimen under a predetermined depth of water;
measuring the static pressure of the test fluid over a test period to create a multiplicity of test measurements;
recording the multiplicity of test measurements to create a test data set;
analyzing the test data set to determine a test result; and
reporting the test result,
the step of analyzing the test data set comprising sub steps of:
creating a validation standard; and
comparing the test data set against the validation standard to determine the test result, the sub step of creating a validation standard comprising testing one or more concrete samples of known quality to produce a validation data set, the validation standard comprising either a threshold value, a slope of a line, or both, derived from the validation data set, and the method further comprising the following steps:
- identifying the concrete test specimen and the test area on an existing concrete structure;
- attaching a system for in situ rapid testing to the concrete test specimen around the test area; and
- using the system for in situ rapid testing to provide the sustained static pressure of the test fluid to the test area.

20. The method according to claim 19, the system for in situ rapid testing comprising:
- a pressure fitting configured and adapted to deliver the test fluid at the sustained static pressure to the test area;
- a gasket configured and adapted to seal the pressure fitting to the outer surface of the concrete test specimen around the test area;
- a support structure configured and adapted to secure the pressure fitting with respect to the outer surface of the concrete test specimen and the gasket under one or more forces created by the sustained static pressure of the test fluid;
- a pressure source configured and adapted to generate the sustained static pressure of the test fluid;
- a plumbing structure configured and adapted to deliver the test fluid from the pressure source to the pressure fitting;
- a pressure measurement device configured and adapted to measure the sustained static pressure of the test fluid, creating a series of pressure measurements over time; and
- a data acquisition module configured and adapted to record the series of pressure measurements over time, the pressure fitting of the system for in situ rapid testing comprising a round pipe flange with a pipe flange sealing surface configured and adapted to compress the gasket against the outer surface of the concrete test specimen around the test area when acted upon by the support structure, the pipe flange sealing surface being a substantially flat surface, a convex surface, or a concave surface, the gasket of the system for in situ rapid testing being configured and adapted to seal against the outer surface of the concrete test specimen around the test area when acted upon by the pressure fitting, the support structure of the system for in situ rapid testing being configured and adapted to transfer a force between the pressure fitting and the concrete test specimen, causing the pressure fitting to compress the gasket against the outer surface of the concrete test specimen around the test area, the round pipe flange of the system for in situ rapid testing having an outer flange diameter, the outer flange diameter being measured in a first plane parallel to the outer surface at a center of the test area when the pipe flange is compressing the gasket, the support structure being contained within a support footprint diameter measurable in the first plane, the support footprint diameter being less than 2 times the outer flange diameter, the support structure comprising one or more fasteners mounted directly in or on a first surface of the concrete test specimen, the first surface of the concrete test specimen being the outer surface of the concrete test specimen or a surface other than the outer surface of the concrete test specimen, and the support structure comprising a clamping member configured and adapted to apply force to the pressure fitting without penetrating or mounting into the concrete test specimen.

* * * * *